United States Patent [19]

Morimoto et al.

[11] Patent Number: 5,128,135
[45] Date of Patent: Jul. 7, 1992

[54] PERCUTANEOUS OR TRANS-MUCOSAL ABSORPTION ENHANCERS, PREPARATIONS CONTAINING THE ENHANCERS, AND A METHOD OF PREPARING THEREOF

[75] Inventors: Yasunori Morimoto; Kenji Sugibayashi, both of Sakado; Seiichi Umeda, Tsurugashima, all of Japan

[73] Assignee: Freund Industrial Co., Ltd., Tokyo, Japan

[21] Appl. No.: 468,374

[22] Filed: Jan. 22, 1990

[30] Foreign Application Priority Data

Jan. 23, 1989 [JP] Japan .................... 1-13474

[51] Int. Cl.⁵ ............................ A61F 13/00
[52] U.S. Cl. ...................... 424/443; 424/447; 424/448; 424/449; 514/690
[58] Field of Search ............. 424/434, 448, 449, 690; 514/946, 947

[56] References Cited

U.S. PATENT DOCUMENTS 4,888,360 12/1989 Leonard et al. ................ 514/675
4,906,486 3/1990 Pera .............................. 424/486

Primary Examiner—Thurman K. Page
Assistant Examiner—Leon R. Horne
Attorney, Agent, or Firm—Kane, Dalsimer, Sullivan, Kurucz, Levy, Eisele and Richard

[57] ABSTRACT

Percutaneous or trans-mucosal absorption enhancer comprising of a terpeneketone and preparation containing thereof. Preferably, the preparation contains a percutaneous or trans-mucosal absorption enhancer in an amount of 0.01–20 weight % of the preparation. In preparing the preparation, a terpeneketone is dissolved and emulsified in a water soluble organic solvent which is medically allowable.

9 Claims, 2 Drawing Sheets

PERCUTANEOUS OR TRANS-MUCOSAL ABSORPTION ENHANCERS, PREPARATIONS CONTAINING THE ENHANCERS, AND A METHOD OF PREPARING THEREOF

BACKGROUND OF THE INVENTION

1. Field of the Invention

The present invention relates to percutaneous or trans-mucosal absorption enhancers and preparations containing said enhancers.

2. Related Art Statement

Conventionally, oral dosage or injection has been widely employed to administer drugs. But, recently percutaneous or trans-mucosal dosage forms have been attracting attentions not only to obtain local effect but also to get systemic effect of the drugs.

Advantages for percutaneous or trans-mucosal medication are as follows:

(1) it is convenient for a patient to apply it at home and to remove promptly if any side effect like toxic symptoms would appear;

(2) it is easily applicable to patients who are incapable of oral administration due to the poor degultion ability, especially to infants and aged persons;

(3) it shows high bioavilability of beneficially effective constituents because it is not subjected to first pass effect (metabolism) at liver which is observed in oral administration;

(4) it is easy to attain sustained release as well as local application, and, both local and systemic effect may be obtained when applied on the local skin diseases such as cancer and herpes; and (5) high patient compliance is obtained with the medication.

Contrary to the advantages as stated above, however, percutaneous or trans-mucosal medication has a big shortcoming that absorption of beneficially effective constituents through skin and mucous membranes is very poor compared with oral administration and injection. Especially when drugs are water soluble, this shortcoming becomes prominent. For enhanced absorption of effective drugs through stratum corneum of the skin, many studies have been done on various percutaneous or trans-musocal absorption enhancers.

Alcohols and glycols; urea derivatives hyaluronic acids; N, N-dimethyl foramide (DMF) and dimethyl sulfoxide (DMSO)), both being non-protic solvents; and surfactants (especially anionic surfactants); have been reported as substances having percutaneous or transmusocal absorption facilitation. The most marked substance in recent years is (1)-dodecylazacycloheptane-2-one (trade name: AZONE) developed by Nelson Co., Ltd., USA.

Among the above enhancers, however, alcohols and glycols are not confirmed to be effective in percutaneous or trans-musocal facilitation and there are many reports expressing that they are ineffective. There are several cumbersome problems for the relation between the enhancing effect and their concentration in preparation. With respect to DMSO its absorption enhancing effect depends largely upon its concentration, and it is considered to be almost ineffective with a concentration lower than 50%. Further it shows adverse effects on eyes and also has side effects on skin, consequently it is not practically used until now. As for urea derivatives, hyaluronic acids, N, N-dimethyl foramide and surfactants, their absorption enhancing effect is remarkably poor as compared with that of dimethyl sulfoxide.

1-dodecylazacycloheptane-2-one shows relatively high absorption enhancing effect even when applied with low concentration but it is a quite novel substance and its safety is not yet confirmed.

Thus percutaneous or trans-mucosal absorption enhancers already known are unsatisfactory in view of the effect and safety so that development of safe and effective absorption enhancers for percutaneous or transmucosal preparation has been demanded increasingly.

SUMMARY OF THE INVENTION

The present inventors have studies percutaneous or trans-mucosal absorption enhances and preparing processes for preparations containing active drugs and such enhancers, and have accomplished the present invention by overcoming the above stated shortcomings.

One of the objects of the present invention is to provide percutaneous or trans-mucosal absorption enhancers which shown excellent absorption-enhancing effect and are reliable in safety.

Another object of the present invention is to provide percutaneous or trans-musocal preparations containing an active drug or drugs and the aforementioned percutaneous or trans-musocal absorption enhancers.

Other objects and the novel characteristics of the present invention together with the above described objects will be more clearly understood according to the detailed explanation and embodiments of the present invention hereinbelow.

Percutaneous or trans-musocal absorption enhances according to the present invention mainly consist of terpeeketones.

Various terpeeketones are available for use including monoterpeneketone, sesquiterpeneketone, diterpeneeketone, etc. With respect to monoterpeneketone, there are l-carvone, piperitone, methone, pulegone, ionone, irone, tagetone, carvomenthone, carvotanacetne, piperitenone and cymeme, etc. As sesquiterpeneketone, there is ciperone, etc., and as for diterpeneeketone there are sugiol, ketomanoyloxide, etc.

Among terpeeketones as listed above, l-carvone, for example, is a main component of spearmint oil, which is contained in tooth paste or food such as chewing gum, drop, etc., as a flavor. With respect to ionone its $LD_{50}$ value was as great as 4590 mg for oral administration in rats, so that it is confirmed to have a very poor toxicity. From actual experiences for use as above, terpeeketones are considered to have little stimulation and toxicity against mucous membrane like mouth and are confirmed to be safe to the skin which shows extremely low stimulation response as compared with mucous membrane.

Tereopeneketones may be used single or in combination with other terpeneketones. Terpeneketones may also be sued together with other percutaneous or transmucosal absorption enhancers already known.

Content of the above-stated terpeneketones contained in a preparation is 0.01-20 weight %, more preferably 0.1-15 weight %. Terpeneketones are generally insoluble water when present singly, so that they had better be dissolved and emulsified by water soluble organic solvents which are medically and pharmaceutically allowable, such as lower alcohol, propylene glycol, glycerol, polyethylene glycol, glycerin fatty acid ester, polyoxyethylene sorbitan fatty acid ester, etc. for preparing the preparations.

As beneficially effective constituents which may be contained in the preparations together with the present invention absorption enhancers for percutaneous or trans-musocal formulations, there are, for example, non-steroidal drugs which are widely used as an antiphlogistic anodyne, hyptoensive drugs, rheumatoid therapeutic drugs, cold syndrome drugs, etc. Varieties of drug formulations may be possible such as cataplasm, ointment, gel, cream, lotion, spray, tape, patch, suppository, etc.

DETAILED DESCRIPTION OF THE PREFERRED EMBODIMENTS

The present invention will be described in detail hereinbelow referring to embodiments.

EXAMPLE 1

Absorption enhancing effect of terpeneketone on the skin permeation indomethacin was tested.

METHOD

An abdominal skin was exercised from a hairless rat (male; body weight of about 150 g) under anesthesia and was set in a two-chamber diffusion cell having a diffusion effective area of 0.636 $cm^2$.

Indomethacin was suspended in an O/W type emulsion containing absorption enhancers as shown in Table 1 below, and 2 ml of the resultant solution was introduced in a cell of the stratum corneum side while 2 ml of physiological saline solution was poured in a cell of the dermis side. With a temperature maintained at 37° C., a part of physiological saline solution in the dermis side cell was sampled predetermined times.

TABLE 1

| | Absorption enhancer | Indo-metha-cin | Tween-20 | Purified water |
|---|---|---|---|---|
| Menthone | 10.0 g | 2.0 g | 0.1 g | 100 g |
| Ionone | 10.0 g | 2.0 g | 0.1 g | 100 g |
| l-carvone | 10.0 g | 2.0 g | 0.1 g | 100 g |
| Piperitone | 10.0 g | 2.0 g | 0.1 g | 100 g |
| Pulegone | 10.0 g | 2.0 g | 0.1 g | 100 g |
| No addition | | 2.0 g | 0.1 g | 100 g |

Determination of indomethacin was carried out by the liquid chromatography (HPLC) in accordance with the conventional method. The results are shown in FIG. 1.

RESULTS

Brief Description of the Drawing

As shown in FIG. 1, all belong to the terpeneketone-added group shows higher skin permeation-enhancing effect of indomethacin than those belonging to not-added group (negative control group). Especially carvone-added group and piperitone-added group are found very effective and their cumulative amounts of skin permeation over 10 hours are as high as about 170 times that of the negative control group.

EXAMPLE 2

Absorption enhancing effect of terpeneketone (l-carvone) on the skin permeation of nicorandil was tested.

METHOD

An abdominal skin excised from a hairless rat and a two-chamber diffusion cell were employed in the same way as in Example 1. In a stratum corneum side cell, nicorandil suspension was pured, which was prepared in a manner that α-carvone was emulsified in water by the use of polysorbate 20 ("Tween 20") and nicroandil was suspended in the resultant solution. As shown in Table 2, 1-dodecylazacycloheptane-2-one (AZONE)-added samples were employed as a positive control group, while terpeneketone-not-added samples were employed as a negative control group.

TABLE 2

| | Absorption enhancer | Nico-randil | Tween-20 | Purified water |
|---|---|---|---|---|
| l-caravone | 3.0 g | 5.0 g | 0.1 g | 100 g |
| AZONE | 3.0 g | 5.0 g | 0.1 g | 100 g |
| No addition | | 5.0 g | 0.1 g | 100 g |

RESULTS

Figure 1:
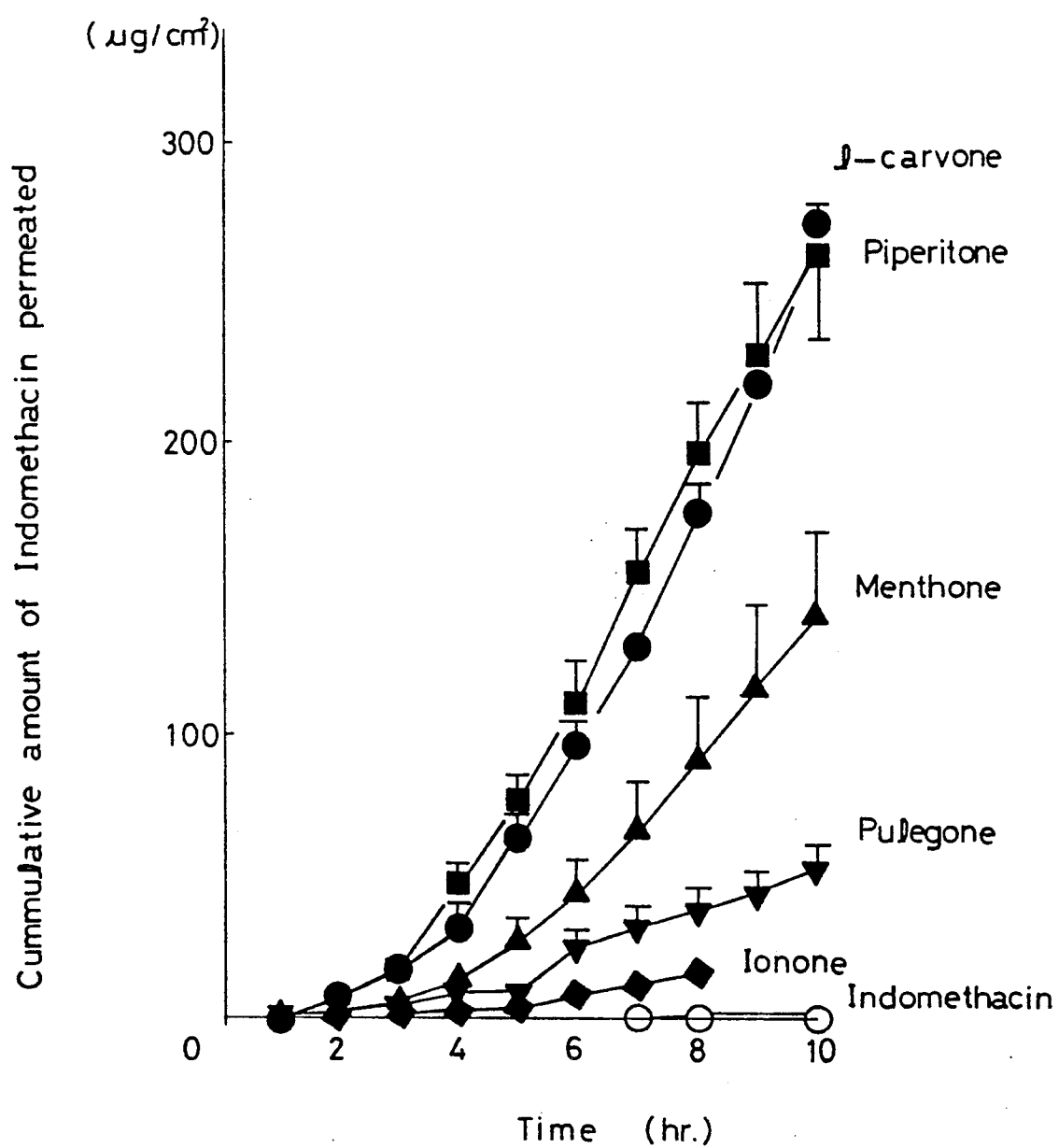
FIG. 1 charts the skin permeation effects of the claimed enhancers.
Figure 2:
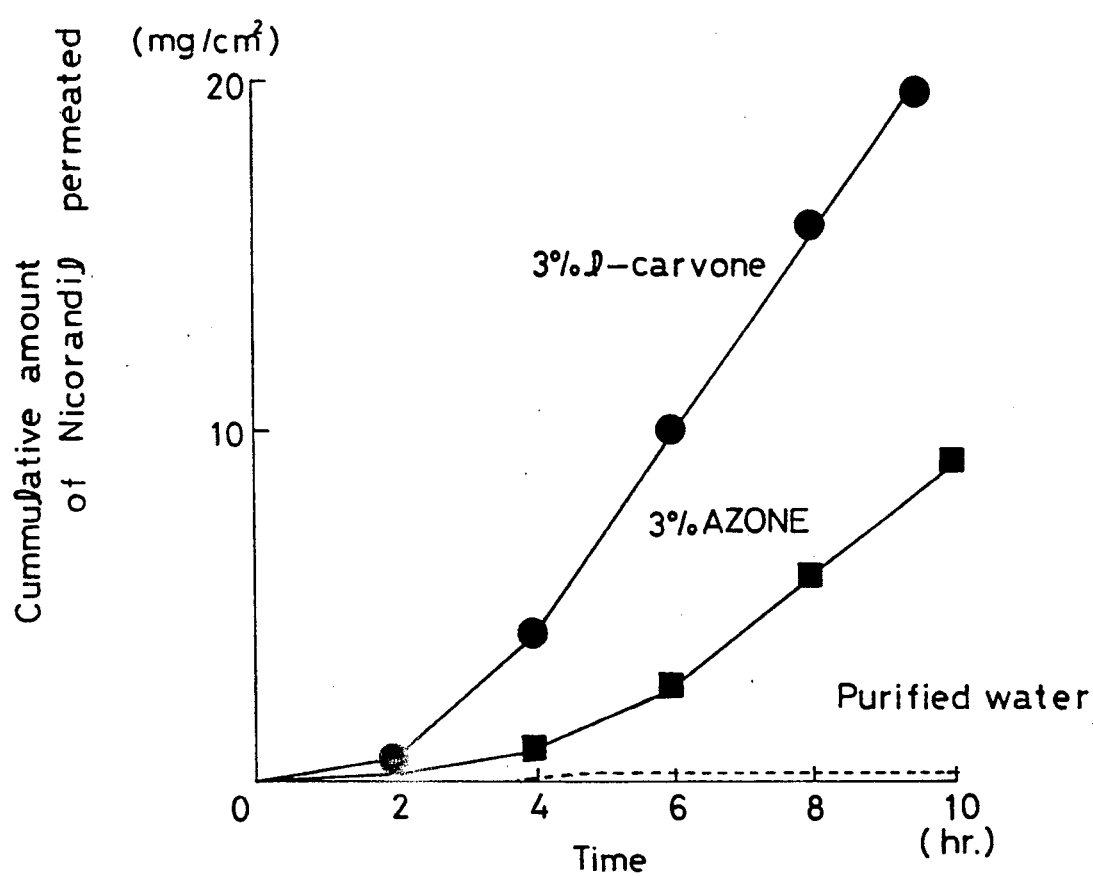
FIG. 2 charts the skin permeation effect of l-carvone.

The results are shown in FIG. 2. As is obvious from the figure, the cumulative amount of skin permeation of nicorandil for α-carvone-added group over 10 hours, for example, is as high as about 140 times that of the negative control group, and is about 1.5 times that of 1-dodecylazacycloheptane-2-one-added group (positive control group), which has been confirmed to have an excellent absorption enhancing effect.

What is claimed is:

1. A pharmaceutical composition for percutaneous or trans-mucosal dosage comprising an effective amount of an active drug selected from the group consisting of non-steroidal drugs in amounts sufficient to be an antiphlogistic anodyne, hypotensive drugs, rheumatoid therapeutic drugs, cold syndrome drugs and piperitone in amounts effective as a percutaneous or trans-musocal absorption enhancer, being formed in a drug formulation selected from the group consisting of cataplasm, ointment, get, cream, lotion, spray, tape, patch and suppository.

2. The composition of claim 1 wherein said percutaneous or tans-musocal absorption enhancer is contained in an amount of 0.01–20 weight percent of the composition.

3. The composition of claim 1 wherein the piperitone is dissolved and emulsified in a water soluble and medically acceptable organic solvent.

4. A method for enhancing the transfer of an active drug through skin or membranes comprising adding piperitone to an active drug selected from the group consisting of non-steroidal drugs used as an antiphlogistic anodyne, hypotensive drugs, rheumatoid therapeutic drugs, cold syndrome drugs and topically applying the mixture.

5. A process for producing a percutaneous or trans-musocal preparation comprising adding piperitone as a percutaneous or trans-musocal absorption enhancer to an effective amount of an active drug selected from the group consisting of non-steroidal drugs used as an antiphlogistic anodyne, hypotensive drugs, rheumatoid therapeutic drugs, cold syndrome drugs.

6. The process of claim 5 wherein the piperitone is dissolved and emulsified in a water soluble and medically acceptable organic solvent.

7. A pharmaceutical composition of claim 1 wherein the active drug is selected from the group consisting of indomethacin and nicorandil, and said percutaneous or trans-mucosal absorption enhancer is contained in an amount of 0.01-20 weight percent of the composition.

8. A method of claim 4 wherein the active drug is selected from the group consisting of indomethacin and nicorandil.

9. A process of claim 5 wherein the active drug is selected from the group consisting of indomethacin and nicorandil.

* * * * *